United States Patent
Sonoyama et al.

(10) Patent No.: US 10,583,070 B2
(45) Date of Patent: Mar. 10, 2020

(54) SOLID POWDER COSMETIC

(71) Applicant: SHISEIDO COMPANY, LTD., Tokyo (JP)

(72) Inventors: Yuji Sonoyama, Kanagawa (JP); Hikari Ohira, Kanagawa (JP); Shun Kubota, Kanagawa (JP); Mariko Akutsu, Kanagawa (JP); Hideo Hata, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 295 days.

(21) Appl. No.: 15/501,196

(22) PCT Filed: Aug. 4, 2015

(86) PCT No.: PCT/JP2015/072115
§ 371 (c)(1),
(2) Date: Feb. 2, 2017

(87) PCT Pub. No.: WO2016/021608
PCT Pub. Date: Feb. 11, 2016

(65) Prior Publication Data
US 2017/0216154 A1 Aug. 3, 2017

(30) Foreign Application Priority Data
Aug. 8, 2014 (JP) .................................. 2014-162570

(51) Int. Cl.
*A61K 8/02* (2006.01)
*A61K 8/19* (2006.01)
*A61K 8/26* (2006.01)
*A61Q 1/12* (2006.01)
*A61K 8/891* (2006.01)
*A61K 8/893* (2006.01)
*A61Q 1/02* (2006.01)
*A61Q 1/10* (2006.01)
*A61Q 1/08* (2006.01)
*A61K 8/27* (2006.01)
*A61K 8/73* (2006.01)

(52) U.S. Cl.
CPC .............. *A61K 8/022* (2013.01); *A61K 8/025* (2013.01); *A61K 8/19* (2013.01); *A61K 8/26* (2013.01); *A61K 8/27* (2013.01); *A61K 8/732* (2013.01); *A61K 8/891* (2013.01); *A61K 8/893* (2013.01); *A61Q 1/02* (2013.01); *A61Q 1/08* (2013.01); *A61Q 1/10* (2013.01); *A61Q 1/12* (2013.01); *A61K 2800/594* (2013.01)

(58) Field of Classification Search
None
See application file for complete search history.

(56) References Cited

U.S. PATENT DOCUMENTS

| | | | | |
|---|---|---|---|---|
| 5,496,544 A | * | 3/1996 | Mellul .................... | A61K 8/891 424/401 |
| 6,171,580 B1 | * | 1/2001 | Katsuyama ............. | A61K 8/27 423/622 |
| 2011/0182846 A1 | * | 7/2011 | Ikeda ........................ | A61K 8/11 424/78.03 |
| 2012/0039830 A1 | * | 2/2012 | Kurahashi ............ | A61K 8/4993 424/63 |
| 2012/0171136 A1 | * | 7/2012 | Sonoyama ............... | A61Q 1/02 424/63 |

FOREIGN PATENT DOCUMENTS

| | | | |
|---|---|---|---|
| EP | 0665273 A1 * | 8/1995 | .............. A61K 8/11 |
| JP | 11279432 A * | 10/1999 | |
| JP | 2002-47139 | 2/2002 | |
| JP | 2003-26538 | 1/2003 | |
| JP | 2006-76982 | 3/2006 | |
| JP | 2006-199644 | 8/2006 | |
| JP | H05-3844 | 8/2006 | |
| JP | 2007-277415 | 10/2007 | |
| JP | 2014-5264 | 1/2014 | |
| JP | 5564256 | 6/2014 | |
| JP | 2014-129279 | 7/2014 | |

OTHER PUBLICATIONS

Ando, A. "Application of synthetic mica to cosmetics." Mineralogical Journal 24.1 (1995): 17-21.*
EP 15829139.3, European Search Report dated Dec. 14, 2017, 7 pages—English.
Database GNPO (Online) Mintel: Oct. 2013 (Oct. 2013), "Powdery Foundation Dressatage", XP002776319, Database Accession No. 2229951 8 pages, www.gnpd.com.
PCT/JP2015/072115, International Search Report and Written Opinion, dated Oct. 27, 2015, 3 pages—English, 7 pages—Japanese.
PCT/JP2015/072115, filed Aug. 4, 2015.
JP 2014-162570, filed Aug. 8, 2014.

* cited by examiner

*Primary Examiner* — Bethany P Barham
*Assistant Examiner* — Peter Anthopolos
(74) *Attorney, Agent, or Firm* — Andrew F. Young, Esq.; Lackenbach Siegel, LLP

(57) ABSTRACT

An objective of the present invention is to provide a solid powder cosmetic excellent in impact resistance and usability despite that boron nitride and spherical resin particle are blended in a large amount. The present invention provides a solid powder cosmetic comprising: 12-30 mass % of synthetic fluorphlogopite iron; 5-15 mass % of boron nitride; and 5-15 mass % of phenyl-modified silicone spherical elastic powder.

14 Claims, No Drawings

SOLID POWDER COSMETIC

RELATED APPLICATIONS

This application claims the priority of and is a § 371 national phase of Ser. No. PCT/JP2015/072115 filed Aug. 5, 2015 the entire contents of which are incorporated herein by reference which in turn claims the priority of Japanese Patent Application No. 2014-162570 filed Aug. 8, 2014, which is incorporated herein by reference.

TECHNICAL FIELD

The present invention relates to a solid powder cosmetic.

BACKGROUND ART

A solid powder cosmetic represented by a powdery foundation is a cosmetic that is formed by adding oil components, as the binder, to powder components, mixing, and then filling and molding in a container. The powder components thereof are mainly inorganic pigments, organic pigments, and resin powder. The pigments are further divided into colored/pearl pigments, which adjust color tone and gloss of cosmetics, and other extender pigments. The representative extender pigments are plate-like powder of talc, mica, kaolin, etc. Such components are the majority of powder components and strongly influence the moldability, adhesion, usability, etc. of cosmetics. The characteristics of powder cosmetics largely depend on characteristic extender pigments such as boron nitride, synthetic fluorphlogopite, and barium sulfate in addition to such basic extender pigments.

Among them, boron nitride has a lubricating property and confers cosmetics with a moderate hiding power and comfortable adhesion; and is thus a component that is desirably blended in a large amount.

In addition, the spherical resin particle of elastic resin, such as silicone elastomer or urethane, is also a component desired to be blended in high quantity because of its good adhesion to the skin and spreadability.

However, it is known that if boron nitride is blended in a large amount, moldability becomes poor and the impact resistance of the cosmetic decreases. If the blending quantity of the spherical elastic resin particle is increased, the moldability becomes poor because of its elasticity and the impact resistance decreases.

Accordingly, if boron nitride and spherical elastic resin particle are blended in large amounts in pursuit of usability, there is an impairment problem with the impact resistance of the solid powder cosmetic.

Concerning such problems, it is reported in Patent Literature 1 that the impact resistance can be improved by adding a dextrin fatty acid ester having a specific structure, due to the ester coating effect, to the formulation in which both boron nitride and spherical silicone elastic particle are contained in large amounts and that a cosmetic excellent in the feeling in use can be obtained. However, dextrin fatty acid esters usable in this method are limited, and it is far from the method of high versatility.

In Patent Literature 2, it is reported that a solid powder cosmetic excellent in impact resistance and usability can be obtained, by treating the surface of some of the extender pigments with a cationic surfactant, even when the extender pigment and spherical elastic resin particle are blended in large amounts. However, this treatment is poorly effective for boron nitride; in addition, it is known that dull color may be generated when an extender pigment treated with a cationic surfactant and a colored pigment such as iron oxide are blended together.

Under such circumstances, a new technology as for the preparation of a solid powder cosmetics has been sought, wherein the large amount of boron nitride and spherical elastic resin particle can be blended while providing an excellent property in usability and, in addition, an impact resistance.

PRIOR ART DOCUMENTS

Patent Literatures

[Patent literature 1] Japanese Unexamined Patent Publication No. 2014-129279
[Patent literature 2] Japanese Unexamined Patent Publication No. 2006-199644
[Patent literature 3] Japanese Patent Publication No. 5564256
[Patent literature 4] Japanese Unexamined Patent Publication No. 1105-3844

SUMMARY OF INVENTION

Technical Problem

The present invention was made in view of the above-described problems of the conventional arts, and an objective is to provide a solid powder cosmetic excellent in impact resistance and usability despite that boron nitride and spherical resin particle are blended in large amounts (specifically, both are 5 mass % or higher).

Solution to Problem

The present inventors have diligently studied to achieve the above objective. As a result, the present inventors have found that a solid powder cosmetic obtained by blending 12-30 mass % of synthetic fluorphlogopite iron, 5-15 mass % of boron nitride, and 5-15 mass % of phenyl-modified silicone spherical elastic powder, relative to the total amount of cosmetic components, has satisfactory impact resistance and excellent usability, and thereby completed the present invention.

That is, the present invention provides a solid powder cosmetic characterized in that it comprises 12-30 mass % of synthetic fluorphlogopite iron, 5-15 mass % of boron nitride, and 5-15 mass % of phenyl-modified silicone spherical elastic powder.

In the solid powder cosmetic of the present invention, additional 0.5-6 mass % of dextrin fatty acid-treated low-temperature-calcined zinc oxide can be suitably blended.

In addition, 15-25 mass % of carboxy silicone soap-treated powder can be suitably blended.

Furthermore, 0.5-6 mass % of stearoxymethylpolysiloxane is preferably blended.

The solid powder cosmetic of the present invention is preferably produced by a wet preparation method, wherein water is used as the main dispersion medium.

Advantageous Effects of Invention

The present invention provides a solid powder cosmetic that is excellent in impact resistance and usability.

DETAILED DESCRIPTION OF THE INVENTION

Hereinafter, the preferred embodiments of the present invention will be explained. Here, "oil components" in this specification include oil and oil-soluble components, and "particle" and "powder" are synonymous. Furthermore, "cosmetic component mixture" means a pulverized mixture of the entire components constituting the cosmetic.

In this specification, the value range that has the lower limit and the upper limit is expressed with the use of a hyphen. For example, "12-30 mass %" means "12 mass % or more and 30 mass % or less".

Synthetic Fluorphlogopite Iron

The synthetic fluorphlogopite iron used in the present invention is not particulary limited as long as it is normally used in cosmetics. However, the average particle size thereof is preferably 2-20 μm and more preferably 5-15 μm, and it is more preferable if the aspect ratio is within the range of 30-80. As such a synthetic fluorphlogopite iron, PDM-FE (manufactured by Topy Industries, Limited), for example, can be listed. For the improvement of dispersion and adhesion, those surface-treated with silicones, fluorine compounds, metal soaps, oil, etc. may be used.

The blending quantity of the synthetic fluorphlogopite iron used in the present invention is preferably 12-30 mass % relative to the total amount of the cosmetic, and more preferably 15-20 mass %. If the blending quantity is less than 12 mass %, smoothness during the use of the cosmetic may be lowered. If the blending quantity exceeds 30 mass %, a lack of powdery texture during use may be lowered.

Boron Nitride

Boron nitride used in the present invention is not particularly limited as long as it is normally used in cosmetics; for example, commercial products such as SHP-3 and SHP-6 (both are manufactured by Mizushima Ferroalloy Co., Ltd.) may be used. For the improvement of dispersion and adhesion, those surface-treated with silicones, fluorine compounds, metal soaps, oil, etc. may be used.

The blending quantity of boron nitride used in the present invention is preferably 5-15 mass %, and more preferably 5-12 mass % relative to the total weight of the solid powder cosmetic. If the blending quantity is less than 5 mass %, the blending effect of boron nitride may not be obtained; if the blending quantity exceeds 15 mass %, impact resistance may become poor.

[Phenyl-Modified Silicone Spherical Elastic Particle]

The phenyl-modified silicone spherical elastic particle used in the present invention is not particularly limited as long as it is normally used in cosmetics. For example, (diphenyl dimethicone/vinyl diphenyl dimethicone/silsesquioxane) crosspolymer (KSP-300, manufactured by Shin-Etsu Chemical Co., Ltd.) etc. can be suitably used.

The blending quantity of phenyl-modified silicone spherical elastic particle used in the present invention is preferably 5-15 mass %, relative to the total weight of the solid powder cosmetic, and more preferably 7-12 mass %. If the blending quantity is less than 5 mass %, the blending effect of phenyl-modified silicone spherical elastic particle may not be obtained; if the blending quantity exceeds 15 mass %, impact resistance may become poor.

[Other Powder Components]

The powder components, blended in the solid powder cosmetic of the present invention, other than the above-described components are not particularly limited as long as they can be used generally. Examples include talc, kaolin, sericite (sericite), muscovite, phlogopite, synthetic mica, synthetic fluorphlogopite, lepidolite, biotite, calcined talc, calcined sericite, calcined muscovite, calcined phlogopite, vermiculite, magnesium carbonate, calcium carbonate, aluminum silicate, barium silicate, calcium silicate, magnesium silicate, strontium silicate, tungstic acid metal salts, magnesium, silica, zeolite, barium sulfate, calcined calcium sulfate (calcined gypsum), calcium phosphate, fluorapatite, hydroxyapatite, ceramic powder, metallic soap (for example, zinc myristate, calcium palmitate, aluminum stearate, etc.), photochromic titanium oxide (titanium dioxide sintered with iron oxide), reduced zinc oxide; organic powders (for example, silicone elastomer powder, silicone powder, silicone resin-coated silicone elastomer powder, polyamide resin powder (nylon powder), polyethylene powder, polystyrene powder, styrene-acrylic acid copolymer resin powder, benzoguanamine resin powder, polytetrafluoroethylene powder, cellulose powder, etc.); inorganic white pigments (for example, titanium dioxide, zinc oxide, etc.); inorganic red pigments (for example, iron oxide (bengala), iron titanate, etc.); inorganic brown pigments (for example, γ-iron oxide etc.); inorganic yellow pigments (for example, yellow iron oxide, yellow ocher, etc.); inorganic black pigments (for example, black iron oxide, low-order titanium oxide, etc.); inorganic violet pigments (for example, mango violet, cobalt violet, etc.); inorganic green pigments (for example, chromium oxide, chromium hydroxide, cobalt titanate, etc.); inorganic blue pigments (for example, ultramarine, Prussian blue, etc.); pearl pigments (for example, bismuth oxychloride, fish scale flake, mica titanium, iron oxide-coated mica titanium, low-order titanium oxide-coated mica titanium, photochromic mica titanium, those in which talc, glass, synthetic fluorphlogopite, silica, bismuth oxychloride, etc. is used instead of mica as the substrate, those in which low-order titanium oxide, colored titanium oxide, iron oxide, alumina, silica, zirconia, zinc oxide, cobalt oxide, aluminum, etc. in addition to titanium oxide are coated as the coating material, that in which resin particles are coated on the surface of pearl pigment as the functional pearl pigment (Japanese Unexamined Patent Publication No. H11-92688), that in which aluminum hydroxide particles are coated on the surface of pearl pigment (Japanese Unexamined Patent Publication No. 2002-146238), that in which zinc oxide particles are coated on the surface of pearl pigment (Japanese Unexamined Patent Publication No. 2003-261421), that in which barium sulfate particles are coated on the surface of pearl pigment (Japanese Unexamined Patent Publication No. 2003-61229), etc.); metal powder pigments (for example, aluminum powder, copper powder, etc.); organic pigments such as zirconium, barium, or aluminum lakes (for example, organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404; and Red No. 3. Red No. 104, Red No. 106, Red No. 227, Red No. 230, Red No. 401, Red No. 505, Orange No. 205, Yellow No. 4, Yellow No. 5, Yellow No. 202, Yellow No. 203, Green No, 3, Blue No. 1, etc.); and natural dyes (for example, chlorophyll, β-carotene, etc.).

Among the above listed components, if 0.5-6 mass % of a dextrin fatty acid-treated low-temperature-calcined zinc oxide (especially preferably, dextrin palmitate-treated zinc oxide) is added, in particular, a cosmetic excellent in makeup lasting can be obtained; thus it is desirable. The dextrin fatty acid-treated low-temperature-calcined zinc oxide can be produced, for example, by coating a fatty acid on the low-temperature-calcined zinc oxide with the use of the method described in Patent Literature 4.

According to the present invention, it is preferable to contain hydrophobic powder and/or hydrophobized powder which can be blended in a large amount. The hydrophobic powder or hydrophobized powder used in the present invention means powder having low affinity to water. The hydrophobic powder is the powder that has low affinity to water as it is, and the hydrophobized powder is the powder in which hydrophobicity is conferred by the surface treatment of the powder having high affinity to water. Here, the "hydrophobicity" is evaluated by the following method and determined. That is, 50 g of ion-exchanged water and 0.1 g of powder to be evaluated are placed in a transparent sealed container, stored at 50° C. for 1 day, and then the visual observation is carried out. If most of the powder to be evaluated is present on the surface of ion-exchanged water, it is evaluated to be "hydrophobic".

As the hydrophobization treatment of powder, the surface of powder can be treated with, for example, higher fatty acids, metal soaps, oils and fats, waxes, silicone compounds, fluorine compounds, hydrocarbons, surfactants, dextrin fatty acid esters, etc. Among such treatments, the treatment with a silicone compound is preferable. In particular, it is preferable to blend a powder of which surface has been treated with a carboxy silicone soap (i.e., metal salt of the terminal carboxyl group of carboxy-modified silicone, referring to Japanese Patent Publication 5564256) in a large amount (as a benchmark, 15-25 mass % of the total amount of a cosmetic), because the impact resistance of the cosmetic is further increased.

The blending quantity of hydrophobic powder and/or hydrophobized powder is preferably 40-100 mass % relative to the total amount of powder in the cosmetic (i.e., powder portion), more preferably 50-90 mass %, and most preferably 60-80 mass %.

[Oil Components]

The oil components blended in the solid powder cosmetic of the present invention are not particularly limited as long as they can be used generally. Specifically, liquid oils and fats, solid oils and fats, waxes, hydrocarbons, higher fatty acids, higher alcohols, synthetic ester oils, silicone oils, etc. can be listed. In this specification, both oil and oil-soluble components are called "oil components".

In the following explanation, POE is the abbreviation of polyoxyethylene and POP is the abbreviation of polyoxypropylene, and the number in the parentheses after POE or POP represents the average addition mole number of POE groups or POP groups in the compound.

Examples of liquid oils and fats include avocado oil, camellia oil, turtle oil, macadamia nut oil, corn oil, mink oil, olive oil, rape seed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, china paulownia oil, Japanese tung oil, jojoba oil, germ oil, and triglycerin.

Examples of solid oils and fats include cacao butter, coconut oil, horse fat, hydrogenated coconut oil, palm oil, beef tallow, mutton tallow, hydrogenated beef tallow, palm kernel oil, lard, beef bone fat, Japan wax kernel oil, hydrogenated oil, beef leg tallow, Japan wax, and hydrogenated castor oil.

Examples of waxes include beeswax, candelilla wax, cotton wax, carnauba wax, bayberry wax, ibota wax, whale wax, montan wax, rice bran wax, lanolin, kapok wax, acetylated lanolin, liquid lanolin, sugarcane wax, isopropyl lanolin fatty acid, hexyl laurate, hydrogenated lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of hydrocarbon oils include liquid paraffin, ozokerite, squalane, pristane, paraffin, ceresin, squalene, petrolatum, and microcrystalline wax.

Examples of higher fatty acids include laurie acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA).

Examples of higher alcohols include linear alcohols (for example, lauryl alcohol, cetyl alcohol, stearyl alcohol, behenyl alcohol, myristyl alcohol, oleyl alcohol, cetostearyl alcohol, etc.); and branched-chain alcohols (for example, stearyl monoglyceride (batyl alcohol), 2-decyltetradecynol, lanolin alcohol, cholesterol, phytosterol, hexyldodecanol, isostearyl alcohol, octyldodecanol, etc.).

Examples of synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, eholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythritol tetra-2-ethylhexanoate, glycerin tri-2-ethylhexanoate, glycerin trioctanoate, glycerin triisopalmitate, trimethylolpropane triisostearate, cetyl 2-ethylhexanoate, 2-ethylhexyl palmitate, glycerin trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of silicone oils include dimethylpolysiloxane, methylhydrogenpolysiloxane, methylphenylpolysiloxane, stearoxymethylpolysiloxane, polyether-modified organopolysiloxane, fluoroalkyl/polyoxyalkylene co-modified organopolysiloxane, alkyl-modified organopolysiloxane, non-terminal-modified organopolysiloxane, fluorine-modified organopolysiloxane, amino-modified organopolysiloxane, silicone gel, acrylic silicone, trimethylsiloxysilicic acid, and silicone compounds such as silicone RTV rubber.

Among them, for the further improvement of usability and impact resistance, silicone wax that is solid or pasty at 25° C. is preferable. Especially preferable examples include acrylic silicone (for example, KP561P: (acrylates/stearyl acrylate/dimethicone methacrylate) copolymer, KP562P: (acrylates/behenyl acrylate/dimethicone methacrylate) copolymer, both are manufactured by Shin-Etsu Chemical Co., Ltd.) and stearoxymethylpolysiloxane (INCI name: (stearoxy methicone/dimethicone) copolymer) (for example, KF7002, manufactured by Shin-Etsu Chemical Co., Ltd.). Among them, if 0.5-6 mass % of stearoxymethylpolysiloxane is blended, usability and impact resistance can be further improved.

The desirable blending quantity of oil components is 0.5-40 mass % relative to the total amount of the cosmetic, preferably 5-30 mass %, and especially preferably 10-25 mass %.

[Other Components]

In the solid powder cosmetic of the present invention, within the range that the effect of the present invention is not impaired, other components, for example, esters, anionic surfactants, cationic surfactants, amphoteric surfactants, nonionic surfactants, moisturizers, water-soluble polymers, thickeners, film-forming agents, UV absorbers, metal ion sequestering agents, lower alcohols, polyhydric alcohols, saccharides, amino acids, organic amines, polymer emulsions, pH adjusters, skin nutrients, vitamins, antioxidants, antioxidant aids, perfumes, water, etc. can be suitably blended as necessary, and the cosmetic can be produced by the ordinary method according to the intended product form.

Hereinafter, specific blendable components will be listed; a solid powder cosmetic can be prepared by blending the above-described essential blending components and one or more of any of the below-described components.

Examples of anionic surfactants include fatty acid soaps (for example, sodium laurate, sodium palmitate, etc.); higher alkyl sulfate ester salts (for example, sodium lauryl sulfate, potassium lauryl sulfate, etc.); alkyl ether sulfate ester salts (for example, POE-lauryl sulfate triethanolamine, sodium POE-lauryl sulfate, etc.); N-acyl sarcosine acid (for example, sodium lauroyl sarcosinate etc.); higher fatty acid amide sulfonic acid salts (for example, sodium N-myristoyl-N-methyltaurine, sodium coconut oil fatty acid methyl tauride, sodium lauryl methyl tauride, etc.); phosphoric acid ester salts (sodium POE-oleyl ether phosphate, POE-stearyl ether phosphoric acid, etc.); sulfosuccinic acid salts (for example, sodium di-2-ethylhexyl sulfosuccinate, sodium monolauroylmonoethanolamide polyoxyethylene sulfosuccinate, sodium lauryl polypropylene glycol sulfosuccinate, etc.); alkylbenzenesulfonic acid salts (for example, linear sodium dodecylbenzenesulfonate, linear dodecylbenzenesulfonic acid triethanolamine, linear dodecylbenzenesulfonic acid, etc.); higher fatty acid ester sulfate ester salts (for example, sodium hydrogenated coconut oil fatty acid glycerin sulfate etc.); N-acyl glutamic acid salts (for example, monosodium N-lauroyl glutamate, disodium N-stearoyl glutamate, monosodium N-myristoyl-L-glutamate, etc.); sulfated oils (for example, turkey red oil etc.); POE-alkyl ether carboxylic acid; POE-alkylaryl ether carboxylic acid salts; α-olefinsulfonic acid salts; higher fatty acid ester sulfonic acid salts; secondary alcohol sulfate ester salts; higher fatty acid alkylolamide sulfate ester salts; sodium lauroyl monoethanolamide succinate; ditriethanolamine N-palmitoyl aspartate; and sodium caseinate.

Examples of cationic surfactants include alkyltrimethylammonium salts (for example, stearyltrimethylammonium chloride, lauryltrimethylammonium chloride, etc.); alkylpyridinium salts (for example, cetylpyridinium chloride etc.); distearyldimethylammonium chloride; dialkyldimethylammonium salts; poly(N,N'-dimethyl-3,5-methylene piperidinium chloride); alkyl quaternary ammonium salts; alkyldimethylbenzylammonium salts; alkylisoquinolinium salts; dialkylmorpholinium salts; POE-alkylamine; alkylamine salts; polyamine fatty acid derivatives; amyl alcohol fatty acid derivatives; benzalkonium chloride; and benzethonium chloride.

Examples of amphoteric surfactants include imidazoline-type amphoteric surfactants (for example, sodium 2-undecyl-N,N,N-(hydroxyethylcarboxymethyl)-2-imidazoline, 2-cocoyl-2-imidazolinium hydroxide-1-carboxyethyloxy disodium salt, etc.); and betaine-type surfactants (for example, 2-heptadecyl-N-carboxymethyl-N-hydroxyethyl-imidazolinium betaine, lauryl dimethylamino acetic acid betaine, alkylbetaines, amidobetaines, sulfobetaines, etc.).

Examples of lipophilic nonionic surfactants include sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, diglycerol sorbitan tetra-2-ethylhexylate, etc.); glycerin polyglycerin fatty acids (for example, glycerin mono-cotton seed oil fatty acid, glycerin monoerucate, glycerin sesquioleate, glycerin monostearate, glycerin α,α'-oleate pyroglutamate, glycerin monostearate malate, etc.); propylene glycol fatty acid esters (for example, propylene glycol monostearate etc.); hydrogenated castor oil derivatives; and glycerin alkyl ethers.

Examples of hydrophilic nonionic surfactants include POE-sorbitan fatty acid esters (for example, POE-sorbitan monooleate, POE-sorbitan monostearate, POE-sorbitan monooleate, POE-sorbitan tetraoleate, etc.); POE sorbit fatty acid esters (for example, POE-sorbit monolaurate, POE-sorbit monooleate, POE-sorbit pentaoleate, POE-sorbit monostearate, etc.); POE-glycerin fatty acid esters (for example, POE-glycerin monostearate, POE-glycerin monoisostearate, POE-glycerin triisostearate, etc.); POE-fatty acid esters (for example, POE-distearate, POE-monodioleate, ethylene glycol distearate, etc.); POE-alkyl ethers (for example, POE-lauryl ether, POE-oleyl ether, POE-stearyl ether, POE-behenyl ether, POE-2-octyldodecyl ether, POE-cholestanol ether, etc.); Pluronic types (for example, Pluronic etc.); POE/POP-alkyl ethers (for example, POE/POP-cetyl ether, POE/POP-2-decyltetradecyl ether, POE/POP-monobutyl ether, POE/POP-hydrogenated lanolin, POE/POP-glycerin ether, etc.); tetraPOE/tetraPOP-ethylenediamine condensation products (for example, Tetronic etc.); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, POE-hydrogenated castor oil maleate, etc.); POE-beeswax/lanolin derivatives (for example, POE-sorbit beeswax etc.); alkanolamides (for example, coconut oil fatty acid diethanolamide, lauric acid monoethanolamide, fatty acid isopropanolamide, etc.); POE-propylene glycol fatty acid esters; POE-alkylamines; POE-fatty acid amides; sucrose fatty acid esters; alkylethoxydimethylamine oxides; and trioleyl phosphate.

Examples of moisturizers include polyethylene glycol, propylene glycol, glycerin, 1,3-butylene glycol, xylitol, sorbitol, maltitol, chondroitin sulfate, hyaluronic acid, mucoitin sulfate, charonin acid, atelocollagen, cholesteryl 12-hydroxystearate, sodium lactate, bile salt, dl-pyrrolidone carboxylic acid salts, alkylene oxide derivatives, short-chain soluble collagen, diglycerin (EO)PO adducts, chestnut rose extract, yarrow extract, and melilot extract.

Examples of natural water-soluble polymers include plant polymers (for example, gum arabic, tragacanth gum, galactan, guar gum, carob gum, karaya gum, carrageenan, pectin, agar, quince seed (marmelo), algecolloid (brown algae extract), starch (rice, corn, potato, wheat), glycyrrhizic acid); microbial polymers (for example, xanthan gum, dextran, succinoglucan, pullulan, etc.); and animal polymers (for example, collagen, casein, albumin, gelatin, etc.).

Examples of semisynthetic water-soluble polymers include starch-based polymers (for example, carboxymethyl starch, methylhydroxypropyl starch, etc.); cellulose-based polymers (methylcellulose, ethylcellulose, methylhydroxypropylcellulose, hydroxyethylcellulose, sodium cellulose sulfate, hydroxypropylcellulose, carboxymethylcellulose, sodium carboxymethylcellulose, crystalline cellulose, cellulose powder, etc.); alginic acid-based polymers (for example, sodium alginate, alginic acid propylene glycol ester, etc.).

Examples of synthetic water-soluble polymers include vinyl polymers (for example, polyvinyl alcohol, polyvinyl methyl ether, polyvinylpyrrolidone, carboxyvinyl polymer, etc.); polyoxyethylene polymers (for example, polyoxyethylene-polyoxypropylene copolymer of polyethylene glycol 20,000, 40,000, or 60,000); acrylic polymers (for example, sodium polyacrylate, polyethyl acrylate, polyacrylamide, etc.); polyethyleneimine; and cationic polymers.

Examples of thickeners include gum arabic, carrageenan, karaya gum, tragacanth gum, carob gum, quince seed (marmelo), casein, dextrin, gelatin, sodium pectate, sodium alginate, methylcellulose, ethylcellulose, CMC, hydroxyethylcellulose, hydroxypropylcellulose, PVA, PVM, PVP, sodium polyacrylate, carboxyvinyl polymer, locust bean gum, guar gum, tamarind gum, dialkyldimethylammonium cellulose sulfate, xanthan gum, aluminum magnesium silicate, bentonite, hectorite, AlMg silicate (Veegum), Laponite, and silicic anhydride.

Examples of UV absorbers include benzoic acid-based UV absorbers (for example, para-aminobenzoic acid (hereinafter, abbreviated as PABA). PABA monoglycerin ester. N,N-dipropoxyPABA ethyl ester, N,N-diethoxyPABA ethyl ester, N,N-dimethylPABA ethyl ester, N,N-dimethylPABA butyl ester, N,N-dimethylPABA ethyl ester, etc.); anthranilic acid-based UV absorbers (for example, homomenthyl N-acetylanthranilate etc.); salicylic acid-based UV absorbers (for example, amyl salicylate, menthyl salicylate, homomenthyl salicylate, octyl salicylate, phenyl salicylate, benzyl salicylate, p-isopropanolphenyl salicylate, etc.); cinnamic acid-based UV absorbers (for example, octyl methoxycinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate, glyceryl mono-2-ethylhexanoyl-diparamethoxycinnamate, etc.); benzophenone-based UV absorbers (for example, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, etc.); 3-(4'-methylbenzylidene)-d,l-camphor, 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenylbenzotriazole; dibenzaladine; dianisoylmethane; 4-methoxy-4'-t-butyldibenzoylmethane; 5-(3,3-dimethyl-2-norbornylidene)-3-pentane-2-one; dimorpholino-pyridazinone; 2-ethylhexyl-2-cyano-3,3-diphenyl acrylate; and 2,4-bis-{[4-(2-ethylhexyloxy)-2-hydroxy]-phenyl}-6-(4-methoxyphenyl)-(1,3,5)-triazine.

Examples of metal ion sequestering agents include 1-hydroxyethane-1,1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediamine hydroxyethyl triacetate.

Examples of lower alcohols include ethanol, propanol, isopropanol, isobutyl alcohol, and t-butyl alcohol.

Examples of polyhydric alcohols include dihydric alcohols (for example, ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, etc.); trihydric alcohols (for example, glycerin, trimethylolpropane, 1,2,6-hexanetriol, etc.); tetrahydric alcohols (for example, pentaerythritol, etc.); pentahydric alcohols (for example, xylitol etc.); hexahydric alcohols (for example, sorbitol, mannitol, etc.); polyhydric alcohol polymers (for example, diethylene glycol, dipropylene glycol, triethylene glycol, polypropylene glycol, tetraethylene glycol, diglycerin, polyethylene glycol, triglycerin, tetraglycerin, polyglycerin, etc.); dihydric alcohol alkyl ethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, etc.); dihydric alcohol alkyl ethers (for example, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, etc.); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, etc.); glycerin monoalkyl ethers (for example, chimyl alcohol, selachyl alcohol, batyl alcohol, etc.); sugar alcohols (for example, sorbitol, maltitol, maltotriose, mannitol, sucrose, erythritol, glucose, fructose, starch degradation sugar, maltose, xylitose, starch degradation sugar reducing alcohol, etc.); Glysolid; tetrahydrofurfuryl alcohol; POE-tetrahydrofurfuryl alcohol; POP-butyl ether; POP/POE-butyl ether; tripolyoxypropylene glycerin ether; POP-glycerin ether; POP-glycerin ether phosphate; POPIPOE-pentaneerythritol ether, and polyglycerin.

Examples of monosaccharides include triose (for example, D-glyceraldehyde, dihydroxyacetone, etc.); tetrose (for example, D-erythrose, D-erythrulose, D-threose, erythritol, etc.); pentose (for example, L-arabinose, D-xylose, L-lyxose, D-arabinose, D-ribose, D-ribulose, D-xylulose, L-xylulose, etc.); hexose (for example, D-glucose, D-talose, D-psicose, D-galactose, D-fructose, L-galactose, L-mannose, D-tagatose, etc.); heptose (for example, aldoheptose, heplose, etc.); octose (for example, octulose etc.); deoxy sugars (for example, 2-deoxy-D-ribose, 6-deoxy-L-galactose, 6-deoxy-L-mannose, etc.); amino sugars (for example, D-glucosamine, D-galactosamine, sialic acid, aminouronic acid, muramic acid, etc.); uronic acid (for example, D-glucuronic acid, D-mannuronic acid, L-guluronic acid, D-galacturonic acid, L-iduronic acid, etc.).

Examples of oligosaccharides include sucrose, gentianose, umbelliferose, lactose, planteose, isolichnoses, α,α-trehalose, raffinose, lichnoses, umbilicine, stachyose, and verbascose.

Examples of polysaccharides include cellulose, quince seed, chondroitin sulfate, starch, galactan, dermatan sulfate, glycogen, gum arabic, heparan sulfate, hyaluronic acid, tragacanth gum, keratan sulfate, chondroitin, xanthan gum, mucoitin sulfate, guar gum, dextran, keratosulfate, locust bean gum, succinoglucan, and charonin acid.

Examples of amino acids include neutral amino acids (for example, threonine, cysteine, etc.); and basic amino acids (for example, hydroxylysine etc.). Examples of amino acid derivatives include sodium acyl sarcosinate (sodium lauroyl sarcosinate), acyl glutamic acid salts, sodium acyl β-alanine, glutathione, and pyrrolidone carboxylic acid.

Examples of organic amines include monoethanolamine, diethanolamine, triethanolamine, morpholine, triisopropanolamine, 2-amino-2-methyl-1,3-propanediol, and 2-amino-2-methyl-1-propanol.

Examples of polymer emulsions include acrylic resin emulsion, polyethyl acrylate emulsion, acrylic resin solution, polyacryl alkyl ester emulsion, polyvinyl acetate resin emulsion, and natural rubber latex.

Examples of pH adjusters include buffers such as lactic acid-sodium lactate, citric acid-sodium citrate, and succinic acid-sodium succinate.

Examples of vitamins include vitamins A, B1, B2, B6, C, E, and derivatives thereof, pantothenic acid and derivatives thereof, and biotin.

Examples of antioxidants include tocopherols, dibutylhydroxytoluene, butylhydroxyanisole, and gallic acid esters.

Examples of antioxidant aids include phosphoric acid, citric acid, ascorbic acid, maleic acid, malonic acid, succinic acid, fumaric acid, cephalin, hexametaphosphate, phytic acid, and ethylenediaminetetraacetic acid.

Examples of other blendable components include preservatives (ethyl paraben, butyl paraben, chlorphenesin, phenoxyethanol, etc.); anti-inflammatory agents (for example, glycyrrhizic acid derivatives, glycyrrhetinic acid derivatives, salicylic acid derivatives, hinokitiol, zinc oxide, allantoin, etc.); whitening agents (for example, placenta extract, saxifraga extract, arbutin, etc.); various extracts (for example, phellodendron bark, coptis rhizome, lithospermum root, peony root, swertia herb, birch, sage, loquat, ginseng, aloe, mallow, iris, grape, coix seed, luffa, lily, saffron, cnidium rhizome, ginger, hypericum, ononis, garlic, capsicum, citrus unshiu peel, Angelica acutiloba, seaweed, etc.), activators (for example, royal jelly, photosensitive elements, cholesterol derivatives, etc.); blood circulation promoters (for example, 4-hydroxy-3-methoxybenzyl nonylic acid amide, nicotinic acid benzyl ester, nicotinic acid β-butoxyethyl ester, capsaicin, zingerone, cantharides tincture, ichthammol, tannic acid, α-borneol, tocopherol nicotinate, inositol hexanicotinate, cyclandelate, cinnarizine, tolazoline, acetylcholine, verapamil, cepharanthine, γ-oryzanol, etc.); antiseborrheic agents (for example, sulfur, thianthol, etc.); and anti-inflammatory agents (for example, tranexamic acid, thiotaurine, hypotaurine, etc.).

In addition, metal sequestering agents such as disodium edetate, trisodium edetate, sodium citrate, sodium polyphosphate, sodium metaphosphate, gluconic acid, and malic acid;

various galenical extracts such as caffeine, tannin, verapamil, tranexamic acid, and derivatives thereof, licorice, Chinese quince, and shinleaf; medicinal agents such as tocopherol acetate, glycyrrhetinic acid, glycyrrhizic acid, and derivatives thereof or salts thereof; whitening agents such as vitamin C, magnesium ascorbyl phosphate, ascorbic acid glucoside, arbutin, and kojic acid; amino acids such as arginine and lysine, and derivatives thereof; and saccharides such as fructose, mannose, erythritol, trehalose, and xylitol can be suitably blended.

Product forms of the solid powder cosmetic of the present invention can take every product form in the category of powder cosmetics. Specifically, product forms such as foundation, eye shadow, cheek color, body powder, perfume powder, baby powder, pressed powder, deodorant powder, and face powder can be taken.

[Production Method]

The solid powder cosmetic of the present invention is preferably prepared by a wet preparation method, wherein powder components and oil components are added to a volatile dispersion medium, slurried, and filled into a container in a slurry state; and the solvent is removed to achieve solidification. This is because that a solid powder cosmetic with high impact resistance is generally obtained by a wet preparation method rather than a dry preparation method.

Generally, the wet preparation method comprises a slurry preparation process wherein a suitable amount of volatile dispersion medium is added/mixed to a mixture of pulverized powder components, oil components, which are the binder, and (other components if necessary) to make a slurry; a filling process to fill the slurry into a container; and a solvent removal process to remove the solvent from the slurry after filling in the container. Each process will be explained.

<Slurry Preparation Process>

As the slurrying method in which powder components and oil components are mixed in a volatile dispersion medium, there is a method wherein powder components and oil components are dry-mixed/disintegrated in advance with a Henschel mixer (trade name), a pulverizer, etc. and they are added into a volatile dispersion medium and mixed/dispersed with a dispersion mixer, homogenizer, planetary mixer, Combi Mix (trade name), agi homo mixer, two-screw kneader, etc. When an oil that is solid or pasty at 25° C. is contained in the above-described oil components, it is preferable to carry out dry-blending of the oil components, after their melting by heating, with the above-described powder components.

In the slurry preparation process, the quantity ratio of powder components and oil components (mass ratio) is preferably powder components/oil components=60/40-99.5/0.5 though it depends upon the kinds of used oil components and powder components. The amount of volatile dispersion medium, used on this occasion, depends upon the polarity, specific gravity, etc. of the used volatile dispersion medium; thus it cannot be stipulated. However, it is important to secure sufficient flowability during filling and molding, and about a half to two times amount of that of the cosmetic constituent components is commonly used.

<Filling Process>

The slurry produced as described above can be suitably filled into a container such as a metal or resin inner plate by injection filling etc.

<Solvent Removal Process>

The volatile solvent in the slurry, which has been filled in the container, is removed by suction-press molding, and a solid powder cosmetic can be obtained by subsequent appropriate drying with a drier.

The volatile dispersion medium used in the above-described slurry preparation process is preferably a solution wherein 0-30 mass % of water-soluble volatile organic solvent such as ethyl alcohol, acetone, isopropyl alcohol, etc., which is a minor dispersion medium, is blended into water, which is the main dispersion medium. If the blending quantity of the above-described minor dispersion medium is adjusted so that the contact angle of the volatile dispersion medium to the uniform mixture of the entire cosmetic components is 125-135 degrees, the moldability of the above-described mixture becomes better, and the impact resistance of the cosmetic increases, so that it is desirable.

EXAMPLES

Hereinafter, the examples of the present invention will be explained; however, the present invention is not limited by these examples. The quantities in the below-described formulations are in mass %.

Initially, the production method of cosmetics used in the examples and evaluation methods thereof will be explained.

<Production Method of Solid Powder Cosmetic>

Powder components and oil components, which have been melted by heating as necessary, described in the formulations of the table below were mixed with a Henschel mixer and then ground with a pulverizer to obtain a uniform mixture. To the mixture, the equal amount of water (i.e., volatile dispersion medium) was added, and a slurry was obtained by mixing with a dispersion mixer. The slurry was filled into an inner plate, and the solvent was removed by suction, and then drying was carried out to obtain a solid powder cosmetic.

<Evaluation of Solid Powder Cosmetic>

(a) Impact Resistance

A solid powder cosmetic was placed in a cosmetic container such as a compact, and the number of times until breakage was examined by dropping it on a metal plate, from the height of 30 cm, in a state that the cosmetic surface is facing downward. The number of test samples were (N)=3 for the same batch. Cosmetics were evaluated to have satisfactory impact resistance if the average drop number was at least 6, and to have excellent impact resistance if the average drop number was 7 or higher.

(b) Usability

Ten expert panelists of cosmetics were asked to apply a solid powder cosmetic on the skin and to evaluate, in 5-scale rating (between very poor usability: 0 and very good usability: 5), for "(on the skin) light spreadability, smoothness, and a lack of powdery texture". The average evaluation value was calculated, and the judgement was made as described below and shown with symbols in the table.

Judgement

A: The average evaluation value is four or more.
B: The average evaluation value is three or more and less than four.
D: The average evaluation value is two or more and less than three.
E: The average evaluation value is less than two.

(c) Evaluation of Makeup Lasting

Ten expert panelists of cosmetics were asked to apply a solid powder cosmetic on the skin. After 3 hours, three expert evaluators were asked to evaluate in 10-scale rating (between very poor makeup lasting: 0 and very good makeup lasting: 10) for each evaluation item "wrinkling evaluation" and "shininess evaluation" based on the below-described evaluation criteria. The average evaluation value was calculated, and the judgement was made as described below and shown with symbols in the table.

[Judgement]

A: The average evaluation value is nine or more.
B: The average evaluation value is six or more and less than nine.
C: The average evaluation value is four or more and less than six.
D: The average evaluation value is two or more and less than four.
E: The average evaluation value is less than two.

(d) Hardness

The level of needle penetration from the surface of each molded product was measured with the Olsen hardness tester (manufactured by Ueshima Seisakusho Co., Ltd.), the average value for the number of tests (N)=5 was calculated. The average value is preferably within the range of 30-100.

In the present specification, the symbols below represent the following states.

A: Excellent
B: Good
C: Acceptable
D: Unacceptable
E: Bad

The compounds used in the following test examples and examples are as follows.

1: PDM-FE (manufactured by TOPY Industries, Ltd)
2: SHP-3 (manufactured by Mizushima Ferroalloy Co., Ltd.)
3: KSP-300 (manufactured by Shin-Etsu Polymer Co., Ltd.)
4: KF-96A-6cs (manufactured by Shin-Etsu Polymer Co., Ltd.)
5: KF-56A (manufactured by Shin-Etsu Polymer Co., Ltd.)
6: PDM-9WA (manufactured by TOPY Industries, Ltd)
7: SP-500 (manufactured by TORAY Industries, Ltd)
8: KF-7002 (manufactured by Shin-Etsu Polymer Co., Ltd.)
9: PLASTIC POWDER D-400 (manufactured by Toshiki Pigment Co., Ltd.)

Test Example 1

The cosmetics of the formulations described in Table 1 were prepared by using the above-described methods. The results are shown in Table 1.

TABLE 1

| | | Test examples | 1-1 | 1-2 | 1-3 | 1-4 | 1-5 | 1-6 | 1-7 | 1-8 | 1-9 |
|---|---|---|---|---|---|---|---|---|---|---|---|
| Formulation | Powder components | Zinc decyl trisiloxanecarboxylate-treated talc | 23.0 | 23.0 | 18.0 | 23.0 | 20.0 | 28.0 | 23.0 | 23.0 | 30.0 |
| | | Synthetic fluorphlogopite iron*[1] | 20.0 | 20.0 | 20.0 | 20.0 | 20.0 | 10.0 | 20.0 | 20.0 | — |
| | | Muscovite | 10.0 | 10.0 | 10.0 | 15.0 | 8.0 | 20.0 | 20.0 | 10.0 | 30.0 |
| | | Boron nitride*[2] | 10.0 | 10.0 | 10.0 | 5.0 | 15.0 | 10.0 | — | 10.0 | — |
| | | Silicone-treated titanium dioxide (Pigment grade) | 7.0 | 7.0 | 7.0 | 7.0 | 7.0 | 7.0 | 7.0 | 7.0 | 7.0 |
| | | Aluminum stearate-treated titanium oxide (ultrafine particle grade) | 4.0 | 4.0 | 4.0 | 4.0 | 4.0 | 4.0 | 4.0 | 4.0 | 4.0 |
| | | Silicone-treated red iron oxide | 0.6 | 0.6 | 0.6 | 0.6 | 0.6 | 0.6 | 0.6 | 0.6 | 0.6 |
| | | Silicone-treated yellow iron oxide | 2.1 | 2.1 | 2.1 | 2.1 | 2.1 | 2.1 | 2.1 | 2.1 | 2.1 |
| | | Silicone-treated black iron oxide | 0.2 | 0.2 | 0.2 | 0.2 | 0.2 | 0.2 | 0.2 | 0.2 | 0.2 |
| | | Spherical silicone resin-coated phenyl-modified silicone rubber powder*[3] | 10.0 | 5.0 | 15.0 | 10.0 | 10.0 | 5.0 | 10.0 | — | — |
| | | Spherical polymethyl methacrylate | — | 5.0 | — | — | — | — | — | 10.0 | 10.0 |
| | | Chlorphenesin | 0.1 | 0.1 | 0.1 | 0.1 | 0.1 | 0.1 | 0.1 | 0.1 | 0.1 |
| | Oil components | Dimethylpolysiloxane*[4] | 3.0 | 3.0 | 3.0 | 3.0 | 3.0 | 3.0 | 3.0 | 3.0 | 3.0 |
| | | Methyl phenyl polysiloxane*[5] | 1.0 | 1.0 | 1.0 | 1.0 | 1.0 | 1.0 | 1.0 | 1.0 | 1.0 |
| | | Glyceryl tri(2-ethylhexanoate) | 4.0 | 4.0 | 4.0 | 4.0 | 4.0 | 4.0 | 4.0 | 4.0 | 4.0 |
| | | Octyl methoxycinnamate | 5.0 | 5.0 | 5.0 | 5.0 | 5.0 | 5.0 | 5.0 | 5.0 | 5.0 |
| Evaluation | | Impact resistance | 8 | 10 | 7 | 10 | 7 | 5 | 7 | 9 | 7 |
| | | Usability | A | B | A | B | A | D | D | D | E |

As shown in Table 1, a solid powder cosmetic obtained by blending 20 mass % of synthetic fluorphlogopite iron, 5 to 15 mass % of boron nitride, and 5-15 mass % of phenyl-modified silicone spherical elastic powder had satisfactory impact resistance, and the usability was excellent (1-1 to 1-5). On the other hand, in the cosmetic wherein synthetic fluorphlogopite iron was reduced to 10 mass % and muscovite was increased (1-6), the impact resistance was low, powdery texture was felt, and the usability was poor (comparison of Test Examples 1-1, 1-2 and 1-6). The results indicate that the blending effect of synthetic fluorphlogopite iron cannot be replaced by muscovite. As a contributory factor, higher oil absorptiveness of muscovite than that of synthetic fluorphlogopite iron is listed.

Cosmetic (1-7) wherein boron nitride was removed from formulation 1-1 had impact resistance; however, smoothness during use and lightness were not present, powdery texture was also felt, and the usability was not satisfactory. Cosmetic (1-8), wherein spherical silicone resin-coated phenyl-modified silicone rubber powder in formulation 1-1 was replaced with spherical polymethylmethacrylate, had impact resistance; however, smoothness during use and lightness were not present, and the usability was not satisfactory. Cosmetic (1-9), wherein none of synthetic fluorphlogopite iron, boron nitride, and phenyl-modified silicone spherical elastic powder were contained, had impact resistance when compared with cosmetic (1-1), which contained these three components; however, smoothness during use and lightness were hardly present, powdery texture was also felt, and the usability was very poor.

As disclosed in Example 5, the present inventors have confirmed that the effect of the present invention can be obtained by increasing the blending quantity of synthetic fluorphlogopite iron even up to 30 mass %.

Thus, it was clarified that a cosmetic excellent in both usability and impact resistance can be obtained by blending 12-30 mass % of synthetic fluorphlogopite iron to the formulation that contains 5-15 mass % of boron nitride and 5-15 mass % of phenyl-modified silicone spherical elastic powder.

Test Example 2: Blending Effect of Hydrophobized Zinc Oxide

Then, characteristic extender pigments were added and their effect was investigated.

To the formulation of the solid powder cosmetic, four kinds of zinc oxide powder, namely, zinc oxide (without surface treatment), dextrin palmitate-treated low-temperature-calcined zinc oxide (surface-treated by the method described in Patent Literature 4), octyltriethoxysilane-treated low-temperature-calcined zinc oxide, or octyltriethoxysilane-treated zinc oxide was added, and the effect to makeup lasting was investigated. As a result, it was clarified that makeup lasting was the best when dextrin palmitate-treated low-temperature-calcined zinc oxide was added. The results are shown in Table 2.

TABLE 2

| | Test Examples | | 2-1 | 2-2 | 2-3 | 2-4 | 2-5 | 2-6 |
|---|---|---|---|---|---|---|---|---|
| Formulation | Powder components | Branched alkyl-modified silicone (ethoxy-functional group)-treated talc | 12.0 | 12.0 | 12.0 | 12.0 | 12.0 | 12.0 |
| | | Zinc decyl trisiloxanecarboxylate-treated talc | 12.0 | 11.0 | 9.0 | 7.0 | 5.0 | 2.0 |
| | | Dextrin palmitate-treated low-temperature-calcined zinc oxide | — | 1.0 | 3.0 | 5.0 | 7.0 | 10.0 |
| | | Synthetic fluorphlogopite iron*1 | 20.0 | 20.0 | 20.0 | 20.0 | 20.0 | 20.0 |
| | | Synthetic fluorphlogopite*6 | 10.0 | 10.0 | 10.0 | 10.0 | 10.0 | 10.0 |
| | | Boron nitride*2 | 5.0 | 5.0 | 5.0 | 5.0 | 5.0 | 5.0 |
| | | Silicone-treated titanium dioxide (Pigment grade) | 7.0 | 7.0 | 7.0 | 7.0 | 7.0 | 7.0 |
| | | Aluminum stearate-treated titanium oxide (ultrafine particle grade) | 4.0 | 4.0 | 4.0 | 4.0 | 4.0 | 4.0 |
| | | Silicone-treated red iron oxide | 0.6 | 0.6 | 0.6 | 0.6 | 0.6 | 0.6 |
| | | Silicone-treated yellow iron oxide | 2.1 | 2.1 | 2.1 | 2.1 | 2.1 | 2.1 |
| | | Silicone-treated black iron oxide | 0.2 | 0.2 | 0.2 | 0.2 | 0.2 | 0.2 |
| | | Spherical nylon powder*7 | 7.0 | 7.0 | 7.0 | 7.0 | 7.0 | 7.0 |
| | | Spherical silicone resin-coated phenyl-modified silicone rubber powder*3 | 7.0 | 7.0 | 7.0 | 7.0 | 7.0 | 7.0 |
| | | Chlorphenesin | 0.1 | 0.1 | 0.1 | 0.1 | 0.1 | 0.1 |
| | Oil components | Dimethylpolysiloxane*4 | 3.0 | 3.0 | 3.0 | 3.0 | 3.0 | 3.0 |
| | | Methyl phenyl polysiloxane*5 | 1.0 | 1.0 | 1.0 | 1.0 | 1.0 | 1.0 |
| | | Glyceryl tri(2-ethylhexanoate) | 4.0 | 4.0 | 4.0 | 4.0 | 4.0 | 4.0 |
| | | Octyl methoxycinnamate | 5.0 | 5.0 | 5.0 | 5.0 | 5.0 | 5.0 |
| Evaluation | Impact resistance | | A | B | B | B | D | E |
| | Usability | | D | B | B | A | A | A |

From Table 2, it was clarified that makeup lasting becomes better when 0.5-6 mass % of dextrin fatty acid-treated low-temperature-calcined zinc oxide, more preferably 1-5 mass % thereof, is added to the formulation of the solid powder cosmetic of the present invention (formulation containing 12-30 mass % of synthetic fluorphlogopite iron, 5-15 mass % of boron nitride, and 5-15 mass % of phenyl-modified silicone spherical elastic powder).

[Investigation of Oil Components]

The present inventors further investigated the oil that is blended as the oil component. The results are shown in Table 3.

TABLE 3

| | Test Examples | | 3-1 | 3-2 | 3-3 | 3-4 | 3-5 |
|---|---|---|---|---|---|---|---|
| Formulation | Powder components | Branched alkyl-modified silicone (ethoxy-functional group)-treated talc | 23.5 | 23.5 | 23.5 | 23.5 | 23.5 |
| | | Synthetic fluorphlogopite iron*1 | 20.0 | 20.0 | 20.0 | 20.0 | 20.0 |
| | | Synthetic fluorphlogopite*5 | 10.0 | 10.0 | 10.0 | 10.0 | 10.0 |
| | | Boron nitride *2 | 5.0 | 5.0 | 5.0 | 5.0 | 5.0 |
| | | Silicone-treated titanium dioxide (Pigment grade) | 7.0 | 7.0 | 7.0 | 7.0 | 7.0 |
| | | Aluminum stearate-treated titanium oxide (ultrafine particle grade) | 4.0 | 4.0 | 4.0 | 4.0 | 4.0 |
| | | Silicone-treated red iron oxide | 0.6 | 0.6 | 0.6 | 0.6 | 0.6 |
| | | Silicone-treated yellow iron oxide | 2.1 | 2.1 | 2.1 | 2.1 | 2.1 |
| | | Silicone-treated black iron oxide | 0.2 | 0.2 | 0.2 | 0.2 | 0.2 |
| | | Spherical nylon powder*7 | 7.0 | 7.0 | 7.0 | 7.0 | 7.0 |
| | | Spherical silicone resin-coated phenyl-modified silicone rubber powder *3 | 7.0 | 7.0 | 7.0 | 7.0 | 7.0 |
| | | Chlorphenesin | 0.2 | 0.2 | 0.2 | 0.2 | 0.2 |
| | Oil components | Dimethylpolysiloxane*4 | 8.1 | 3.1 | 3.1 | 3.1 | 3.1 |
| | | Vaseline | — | 5.0 | — | — | — |
| | | Microcrystalline wax | — | — | 5.0 | — | — |
| | | Dipentaerythrityl hexaoxystearate | — | — | — | 5.0 | — |
| | | Stearoxymethylpolysiloxane*8 | — | — | — | — | 5.0 |
| | | Methyl phenyl polysiloxane | 1.0 | 1.0 | 1.0 | 1.0 | 1.0 |
| | | Phenoxyethanol | 0.3 | 0.3 | 0.3 | 0.3 | 0.3 |
| | | Glyceryl tri(2-ethylhexanoate) | 4.0 | 4.0 | 4.0 | 4.0 | 4.0 |
| Evaluation | Hardness | | 48 | 44 | 40 | 45 | 45 |
| | Impact resistance | | 7 | 10 | 12 | 12 | 12 |
| | Usability | | A | B | B | B | A |

Table 3, it was found that usability and impact resistance of the solid powder cosmetic of the present invention become better when stearoxymethylpolysiloxane is blended.

Hereinafter, the present invention will be explained by listing more examples; however, the present invention is not limited by these examples. The carboxy silicone soap-treated talc and dextrin palmitate-treated low-temperature-calcined zinc oxide, used in the below examples, were produced by the methods described in Patent Literature 3 and Patent Literature 4, respectively.

Example 2: Powdery Foundation

<Formulation>

| Component | Blending quantity (mass %) |
|---|---|
| (1) Carboxy silicone soap-treated talc | balance |
| (2) Synthetic fluorphlogopite iron*1 | 15.0 |
| (3) Synthetic fluorphlogopite*6 | 10.0 |
| (4) Barium sulfate | 5.0 |
| (5) Boron nitride*2 | 5.0 |
| (6) Aluminum stearate-treated particulate titanium oxide | 4.0 |

-continued

| Component | Blending quantity (mass %) |
|---|---|
| (7) Dextrin palmitate-treated low-temperature-calcined zinc oxide | 2.0 |
| (8) Silicone-treated titanium oxide | 10.0 |
| (9) Silicone-treated red iron oxide | 0.2 |
| (10) Silicone-treated yellow iron oxide | 1.4 |
| (11) Silicone-treated black iron oxide | 2.0 |
| (12) Spherical nylon powder*7 | 6.0 |

-continued

| Component | Blending quantity (mass %) |
|---|---|
| (13) Spherical silicone resin-coated phenyl-modified silicone rubber powder*3 | |
| (14) Spherical urethane powder*9 | 3.0 |
| (15) Chlorphenesin | 0.2 |
| (16) Dimethylpolysiloxane*4 | 2.0 |
| (17) Phenyl trimethicone | 1.0 |
| (18) Octyl methoxycinnamate | 5.0 |
| (19) Stearoxymethylpolysiloxane*8 | 1.0 |
| (20) Phenoxyethanol | 0.3 |

<Preparation Method>

The above-described powder components ((1) to (15)) and oil components ((16) to (20)), which had been melted by heating at 75 degrees, were mixed by stirring with a Henschel mixer, and a uniform mixture was obtained by subsequent grinding with a pulverizer. To the mixture, the equal amount (mass) of water was added, and a slurry was obtained by mixing with a dispersion mixer. The slurry was filled into an inner plate, the solvent was removed by suction press molding, and a powdery foundation was obtained by drying with a warm air drier.

The obtained powdery foundation was excellent in impact resistance and usability.

Example 3: Powdery Foundation

<Formulation>

| Component | Blending quantity (mass %) |
|---|---|
| (1) Carboxy silicone soap-treated talc | balance |
| (2) Synthetic fluorphlogopite iron*[1] | 15.0 |
| (3) Silicone-treated synthetic fluorphlogopite | 10.0 |
| (4) Glass flakes | 5.0 |
| (5) Boron nitride*[2] | 5.0 |
| (6) Aluminum stearate-treated particulate titanium oxide | 4.0 |
| (7) Dextrin palmitate-treated low-temperature-calcined zinc oxide | 2.0 |
| (8) Silicone-treated titanium oxide | 10.0 |
| (9) Silicone-treated red iron oxide | 0.2 |
| (10) Silicone-treated yellow iron oxide | 1.4 |
| (11) Silicone-treated black iron oxide | 2.0 |
| (12) Spherical nylon powder*[7] | 6.0 |
| (13) Spherical silicone resin-coated phenyl-modified silicone rubber powder*[3] | 8.0 |
| (14) Spherical urethane powder*[9] | 3.0 |
| (15) Methylparaben | 0.2 |
| (16) Dimethylpolysiloxane*[4] | 2.0 |
| (17) Phenyl trimethicone | 1.0 |
| (18) Octyl methoxycinnamate | 3.0 |
| (19) Octocrylene | 2.0 |
| (20) Stearoxymethylpolysiloxane*[8] | 1.0 |
| (21) Phenoxyethanol | 0.7 |

<Preparation Method>

The above-described powder components ((1) to (15)) and oil components ((16) to (21)), which had been melted by heating at 75 degrees, were mixed by stirring with a Henschel mixer, and a uniform mixture was obtained by subsequent grinding with a pulverizer. To the mixture, the equal amount (mass) of water was added, and a slurry was obtained by mixing with a dispersion mixer. The slurry was filled into an inner plate, the solvent was removed by suction press molding, and a powdery foundation was obtained by drying with a warm air drier.

The obtained powdery foundation was excellent in impact resistance and usability.

Example 4: Face Powder

<Formulation>

| Component | Blending quantity (mass %) |
|---|---|
| (1) Carboxy silicone soap-treated talc | balance |
| (2) Synthetic fluorphlogopite iron*[1] | 20.0 |
| (3) Silicone-treated sericite | 5.0 |
| (4) Muscovite | 5.0 |
| (5) Boron nitride*[2] | 5.0 |
| (6) Aluminum stearate-treated particulate titanium oxide | 4.0 |
| (7) Dextrin palmitate-treated low-temperature-calcined zinc oxide | 2.0 |
| (8) Silicone-treated titanium oxide | 3.0 |
| (9) Silicone-treated red iron oxide | 0.05 |
| (10) Silicone-treated yellow iron oxide | 0.1 |
| (11) Spherical polymethyl methacrylate | 5.0 |
| (12) Spherical nylon powder*[7] | 6.0 |
| (13) Spherical silicone resin-coated phenyl-modified silicone rubber powder*[3] | 8.0 |
| (14) Spherical urethane powder*[9] | 3.0 |
| (15) Methylparaben | 0.2 |
| (16) Dimethylpolysiloxane*[4] | 2.0 |
| (17) Phenyl trimethicone | 1.0 |
| (18) Diisostearyl malate | 1.0 |
| (19) Cetyl ethylhexanoate | 1.0 |
| (20) Stearoxymethylpolysiloxane*[8] | 1.0 |
| (21) Liquid paraffin | 1.0 |

<Preparation Method>

The above-described powder components ((1) to (15)) and oil components ((16) to (21)), which had been melted by heating at 75 degrees, were mixed by stirring with a Henschel mixer, and a uniform mixture was obtained by subsequent grinding with a pulverizer. To the mixture, the equal amount (mass) of water was added, and a slurry was obtained by mixing with a dispersion mixer. The slurry was filled into an inner plate, the solvent was removed by suction press molding, and a face powder was obtained by drying with a warm air drier.

The obtained face powder was excellent in impact resistance and usability.

Example 5: Powdery Foundation

<Formulation>

| Component | Blending quantity (mass %) |
|---|---|
| (1) Carboxy silicone soap-treated talc | balance |
| (2) Synthetic fluorphlogopite iron*[1] | 30.0 |
| (3) Silicone-treated barium sulfate | 5.0 |
| (4) Boron nitride*[2] | 5.0 |
| (5) Aluminum stearate-treated particulate titanium oxide | 5.0 |
| (6) Dextrin palmitate-treated low-temperature-calcined zinc oxide | 3.0 |
| (7) Silicone-treated titanium oxide | 9.0 |
| (8) Silicone-treated red iron oxide | 0.2 |
| (9) Silicone-treated yellow iron oxide | 1.4 |
| (10) Silicone-treated black iron oxide | 2.0 |
| (11) Spherical nylon powder*[7] | 5.0 |
| (12) Spherical silicone resin-coated phenyl-modified silicone rubber powder*[3] | 6.0 |
| (13) Spherical urethane powder*[9] | 3.0 |
| (14) Chlorphenesin | 0.2 |
| (15) Dimethylpolysiloxane*[4] | 2.0 |
| (16) Caprylic/capric triglyceride | 2.0 |
| (17) Phenyl trimethicone | 1.0 |
| (18) Octyl methoxycinnamate | 5.0 |
| (19) Acrylates/stearyl acrylate/dimethicone methacrylate copolymer (KP561P, manufactured by Shin-Etsu Polymer Co., Ltd.) | 0.7 |
| (20) Stearoxymethylpolysiloxane*[8] | 0.7 |

<Preparation Method>

The above-described powder components ((1) to (14)) and oil components ((15) to (21)), which had been melted by heating at 75 degrees, were mixed by stirring with a Henschel mixer, and a uniform mixture was obtained by subsequent grinding with a pulverizer. To the mixture, the equal amount (mass) of water was added, and a slurry was obtained by mixing with a dispersion mixer. The slurry was filled into an inner plate, the solvent was removed by suction press molding, and a powdery foundation was obtained by drying with a warm air drier.

The obtained powdery foundation was excellent in impact resistance and usability.

What is claimed is:

1. A solid powder cosmetic, comprising:
   12-30 mass % of synthetic fluorphlogopite iron;
   5-15 mass % of boron nitride; and
   5-15 mass % of phenyl-modified silicone spherical elastic powder.

2. The solid powder cosmetic according to claim 1, further comprising: 0.5-6 mass % of dextrin fatty acid-treated low-temperature-calcined zinc oxide.

3. The solid powder cosmetic according to claim 1, further comprising:
   15-25 mass % of carboxy silicone soap-treated powder.

4. The solid powder cosmetic according to claim 1, further comprising:
   0.5-6 mass % of stearoxymethylpolysiloxane.

5. The solid powder cosmetic according to claim 2, further comprising:
   15-25 mass % of carboxy silicone soap-treated powder.

6. The solid powder cosmetic according to claim 2, further comprising:
   0.5-6 mass % of stearoxymethylpolysiloxane.

7. The solid powder cosmetic according to claim 3, further comprising
   0.5-6 mass % of stearoxymethylpolysiloxane.

8. The solid powder cosmetic according to claim 1, wherein: the cosmetic is produced by a wet preparation method using water as a main dispersion medium.

9. The solid powder cosmetic according to claim 2, wherein: the cosmetic is produced by a wet preparation method using water as a main dispersion medium.

10. The solid powder cosmetic according to claim 3, wherein: the cosmetic is produced by a wet preparation method using water as a main dispersion medium.

11. The solid powder cosmetic according to claim 4, wherein: the cosmetic is produced by a wet preparation method using water as a main dispersion medium.

12. The solid powder cosmetic according to claim 5, wherein: the cosmetic is produced by a wet preparation method using water as a main dispersion medium.

13. The solid powder cosmetic according to claim 6, wherein: the cosmetic is produced by a wet preparation method using water as a main dispersion medium.

14. The solid powder cosmetic according to claim 7, wherein: the cosmetic is produced by a wet preparation method using water as a main dispersion medium.

* * * * *